US012758569B2

(12) United States Patent
Sauntharajah et al.

(10) Patent No.: US 12,758,569 B2
(45) Date of Patent: Oct. 13, 2026

(54) TREATMENT OF RNA VIRUS INFECTION WITH A CYTIDINE DEAMINASE INHIBITOR

(71) Applicant: The Cleveland Clinic Foundation, Cleveland, OH (US)

(72) Inventors: Yogen Saunthararajah, Cleveland, OH (US); Babal K. Jha, Cleveland, OH (US); Xiaorong Gu, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 426 days.

(21) Appl. No.: 18/552,615

(22) PCT Filed: Mar. 22, 2022

(86) PCT No.: PCT/US2022/021322
§ 371 (c)(1),
(2) Date: Sep. 26, 2023

(87) PCT Pub. No.: WO2022/204126
PCT Pub. Date: Sep. 29, 2022

(65) Prior Publication Data

US 2024/0197766 A1 Jun. 20, 2024

Related U.S. Application Data

(60) Provisional application No. 63/166,567, filed on Mar. 26, 2021.

(51) Int. Cl.
*A61K 31/7068* (2006.01)
*A61K 31/277* (2006.01)
(Continued)

(52) U.S. Cl.
CPC ........ *A61K 31/7068* (2013.01); *A61K 31/277* (2013.01); *A61K 45/06* (2013.01); *A61P 31/14* (2018.01)

(58) Field of Classification Search
CPC .......................... A61K 31/706; A61K 31/7068
See application file for complete search history.

(56) References Cited

U.S. PATENT DOCUMENTS 4,210,638 A 7/1980 Greer
9,259,469 B2 * 2/2016 Desimone .......... A61K 31/7068
(Continued)

FOREIGN PATENT DOCUMENTS

WO WO-8704929 A1 8/1987
WO WO-9426761 A1 11/1994
(Continued)

OTHER PUBLICATIONS

Yusa et al., "Human Immunodeficiency Virus Type 1 Induces 1-beta-D-Arabinofuranosylcytosine resistance in human H9 Cell Line" Journal of Biological Chemistry vol. 267 No. 24 pp. 16848-16850 (Year: 1992).*
(Continued)

*Primary Examiner* — Andrea Olson
(74) *Attorney, Agent, or Firm* — Jason R. Bond; Casimir Jones, S.C.

(57) ABSTRACT

The present invention provides compositions, systems, kits, and methods for treating a subject with an RNA virus infection (e.g., SARS-COV-2) by administering or providing a composition comprising a cytidine deaminase inhibitor (e.g., tetrahy-drouridine or cedazuridine).

12 Claims, 12 Drawing Sheets

(51) Int. Cl.
*A61K 45/06* (2006.01)
*A61P 31/14* (2006.01)

(56) References Cited

U.S. PATENT DOCUMENTS

| | | | | |
|---|---|---|---|---|
| 9,265,785 | B2 * | 2/2016 | Desimone | A61K 31/7072 |
| 10,517,884 | B2 * | 12/2019 | Desimone | A61P 35/02 |
| 11,096,953 | B2 * | 8/2021 | Desimone | A61P 7/06 |
| 11,376,270 | B2 * | 7/2022 | Saunthararajah | A61P 35/00 |
| 2009/0137521 | A1 | 5/2009 | Hamilton et al. | |
| 2019/0209598 | A1 | 7/2019 | Deans et al. | |
| 2024/0058367 | A1 * | 2/2024 | Desimone | A61P 35/00 |

FOREIGN PATENT DOCUMENTS

| | | | | |
|---|---|---|---|---|
| WO | WO-2005115410 | A2 * | 12/2005 | A61P 31/18 |
| WO | WO-2010075301 | A1 | 7/2010 | |
| WO | WO-2020061135 | A1 | 3/2020 | |
| WO | WO-2021007283 | A1 | 1/2021 | |

OTHER PUBLICATIONS

Ojewole et al., "Exploring the use of novel drug delivery systems for antiretroviral drugs" European Journal of Pharmaceutics and Biopharmaceuticsvol. 70 pp. 697-710, doi:10.1016/j.ejpb.2008.06.020 (Year: 2008).*

Pissinati et al. , "Enteric coating of soft gelatin capsules by spouted bed: effect of operating conditions on coating efficiency and on product quality" European Journal of Pharmaceutics and Biopharmaceutics vol. 55 pp. 313-321, doi: 10.1016/S0939-6411(03)00002-X (Year: 2003).*

Stasi et al., "Treatment for COVID-19: An Overview" European Journal of Pharmacology vol. 889, 173644, DOI:10.1016/j.ejphar.2020.173644 (Year: 2020).*

Parvathaneni et al., "Therapeutic potential of inhalable medications to combat coronavirus disease-2019" Ther Deliv vol. 12 No. 2 pp. 105-110, DOI:10.4155/tde-2020-0092 (Year: 2020).*

Extended European Search Report for European Application No. 22776455.2, mailed Nov. 14, 2024, 10 Pages.

International Search Report and Written Opinion for International Application No. PCT/US2022/21322, mailed Aug. 3, 2022, 12 Pages.

Aduma P. J., et al., "Deoxyribonucleoside Triphosphate Pools of Herpes Simplex Virus Infected Cells: The Influence of Selective Antiherpes Agents and the Role of the Deaminase Pathway", Biochemistry and Cell Biology, May-Jun. 1991, vol. 69, No. 5-6, pp. 409-414.

Aduma P.J., et al., "Regulatory Effects of Deoxyribonucleosides on the Activity of - Methoxymethyl-2'-Deoxycytidine: Modulation of Antiherpes Activity by Deoxyguanosine and Tetrahydrodeoxyuridine", Antiviral Research, May 1991, vol. 15, No. 4, pp. 301-313.

Barnard D.L., et al., "Inhibition of Severe Acute Respiratory Syndrome-Associated Coronavirus (SARSCoV) by Calpain Inhibitors and Beta-D-N4-Hydroxycytidine", Antiviral Chemistry & Chemotherapy, Jan. 2004, vol. 15, No. 1, pp. 15-22.

Bernhoff E., et al., "Leflunomide Inhibition of BK Virus Replication in Renal Tubular Epithelial Cells", Journal of Virology, Feb. 2010, vol. 84, No. 4, pp. 2150-2156.

Beumer J.H., et al., "Plasma Pharmacokinetics and Oral Bioavailability of 3,4,5,6-Tetrahydrouridine, a Cytidine Deaminase Inhibitor, in Mice", Cancer Chemotherapy and Pharmacology, Aug. 2008, vol. 62, No. 3, 457-464, pp. 1-16.

Camarasa M-J., et al., "Uridine 5'-Diphosphate Glucose Analogues. Inhibitors of Protein Glycosylation That Show Antiviral Activity", Journal of Medicinal Chemistry, Jan. 1985, vol. 28, No. 1, pp. 40-46.

Cao B., et al., "A Trial of Lopinavir-ritonavir in Adults Hospitalized With Severe Covid-19," The New England Journal of Medicine, May 7, 2020, vol. 382, No. 19, pp. 1787-1799 (13 Pages), (Mar. 18, 2020).

Chen S., et al., "Suppression of Pyrimidine Biosynthesis by Targeting DHODH Enzyme Robustly Inhibits Rotavirus Replication", Antiviral Research, Apr. 8, 2019, vol. 167, pp. 35-44.

Chong A.S., et al., "Concurrent Antiviral and Immunosuppressive Activities of Leflunomide In Vivo", American Journal of Transplantation, Jan. 2006, vol. 6, No. 1, pp. 69-75.

Chung D., "The Establishment of an Antiviral State by Pyrimidine Synthesis Inhibitor Is Cell Type-Specific", Journal of Antimicrobial Agents, Jan. 2015, vol. 1, No. 1, pp. 1-9.

Chung S.J., et al., "Structure of Human Cytidine Deaminase Bound to a Potent Inhibitor", Journal of Medicinal Chemistry, Jan. 7, 2005, vol. 48, No. 3, pp. 658-660.

Denison M.R., et al., "Coronaviruses: An RNA Proofreading Machine Regulates Replication Fidelity and Diversity", RNA Biology, Mar. 1, 2011, vol. 8, No. 2, pp. 270-279.

Desimone J., et al., "Tetrahydrouridine, Cytidine Analogues, and Hemoglobin F", American Journal of Hematology, Mar. 1985, vol. 18, No. 3, pp. 283-288.

Dover G.J., et al., "5-Azacytidine Increases HbF Production and Reduces Anemia in Sickle Cell Disease: Dose-Response Analysis of Subcutaneous and Oral Dosage Regimens," Blood, Sep. 1985, vol. 66, No. 3, pp. 527-532.

Drappier M., et al., "A Novel Mechanism of RNase L Inhibition: Theiler's Virus L* Protein Prevents 2-5A from Binding to RNase L", PLoS Pathogens, Apr. 13, 2018, vol. 14, No. 4, e1006989., pp. 1-27.

Ferraris D., et al., "Design, Synthesis, and Pharmacological Evaluation of Fluorinated Tetrahydrouridine Derivatives as Inhibitors of Cytidine Deaminase", Journal of Medicinal Chemistry, Feb. 12, 2014, vol. 57, No. 6, pp. 2582-2588.

Gil-Fernandez G., et al., "Antiviral Activity of Uridine 5'-Diphosphate Glucose Analogues Against Some Enveloped Viruses in Cell Culture", Antiviral Research, Oct. 1987, vol. 8, No. 5-6, pp. 299-310.

Goldenthal E.I., et al., "Preclinical Toxicologic Evaluation of Tetrahydrouridine (NSC-112907) in Beagle Dogs and Rhesus Monkeys", Cancer Chemotherapy Reports, Part 3, Sep. 1974, vol. 5, No. 1, pp. 15-16.

Gu X., et al., "Decitabine- and 5-azacytidine Resistance Emerges From Adaptive Responses of the Pyrimidine Metabolism Network," Lukemia, Apr. 2021, vol. 35, No. 4, pp. 1023-1036.

Hagemeijer M.C., et al., "Visualizing Coronavirus RNA Synthesis in Time by Using Click Chemistry", Journal of Virology, May 2012, vol. 86, No. 10, pp. 5808-5816.

Heinemann V., et al., "Modulation of Deoxynucleotide Metabolism by the Deoxycytidylate Deaminase Inhibitor 3,4,5,6-Tetrahydrodeoxyuridine," Biochemical Pharmacology, Nov. 15, 1989, vol. 38, No. 22, pp. 4115-4121.

Ho D.H.W., et al., "Clinical Pharmacology of Tetrahydrouridine", The Journal of Clinical Pharmacology, May-Jun. 1978, vol. 18, No. 5-6, pp. 259-265.

Ho D.H.W., et al., "Effects of Tetrahydrouridine on the Uptake and Metabolism of 1-Beta-D-Arabinofuranosylcytosine in Human Normal and Leukemic Cells", Cancer Research, Jul. 1980, vol. 40, No. 7, pp. 2444-2446.

Hou Y.J., et al., "SARS-CoV-2 Reverse Genetics Reveals a Variable Infection Gradient in the Respiratory Tract", Cell, vol. 182, pp. 429-446 e414, 33 Pages, Jul. 23, 2020, doi:10.1016/j.cell.2020.05.042.

Hussan et al., "A Review on Recent Advances of Enteric Coating", IOSR Journal of Pharmacy, e-ISSN: 2250-3013, p-ISSN: 2319-4219, vol. 2, No. 6, Nov.-Dec. 2012, pp. 5-11.

Jha B.K., et al., "Suppression of Antiviral Innate Immunity by Sunitinib Enhances Oncolytic Virotherapy", Molecular Therapy, Sep. 2013, vol. 21, No. 9, pp. 1749-1757.

John G.T., et al., "A Prospective Evaluation of Leflunomide Therapy for Cytomegalovirus Disease in Renal Transplant Recipients", Transplantation Proceedings, Dec. 2005, vol. 37, No. 10, pp. 4303-4305.

John G.T., et al., "Leflunomide Therapy for Cytomegalovirus Disease in Renal Allograft Recipients", Transplantation, May 15, 2004, vol. 77, No. 9, pp. 1460-1461.

(56) References Cited

OTHER PUBLICATIONS

Knight D.A., et al., "Inhibition of Herpes Simplex Virus Type 1 by the Experimental Immunosuppressive Agent Leflunomide", Transplantation, Jan. 15, 2001, vol. 71, No. 1, pp. 170-174.
Kreis W., et al., "Tetrahydrouridine: Physiologic Disposition and Effect Upon Deamination of Cytosine Arabinoside in Man", Cancer Treatment Reports, Oct. 1977, vol. 61, No. 7, pp. 1347-1353.
Kreis W., et al., "Therapy of Refractory/Relapsed Acute Leukemia with Cytosine Arabinoside Plus Tetrahydrouridine (an Inhibitor of Cytidine Deaminase)—a Pilot Study", Leukemia, Nov. 1991, vol. 5, No. 11, pp. 991-998.
Krol J., et al., "Antiviral Activity of Uridine Derivatives of 2-Deoxy Sugars Against Tick-Borne Encephalitis Virus", Molecules, Mar. 21, 2019, vol. 24, No. 6, 1129, pp. 1-12.
Lavelle D., et al., "Effects of Tetrahydrouridine on Pharmacokinetics and Pharmacodynamics of Oral Decitabine," Blood, Feb. 2, 2012, vol. 119, No. 5, pp. 1240-1247.
Liacini A., et al., "Anti-BK Virus Mechanisms of Sirolimus and Leflunomide Alone and in Combination: Toward a New Therapy for BK Virus Infection", Transplantation, Dec. 27, 2010, vol. 90, No. 12, pp. 1450-1457.
Marsh W., et al., "Therapy of Refractory/Relapsed Acute Myeloid Leukemia and Blast Crisis of Chronic Myeloid Leukemia with the Combination of Cytosine Arabinoside, Tetrahydrouridine, and Carboplatin", Cancer Chemotherapy and Pharmacology, Jan. 1993, vol. 31, No. 6, pp. 481-484.
Molokie R., et al., "Oral Tetrahydrouridine and Decitabine for Non-cytotoxic Epigenetic Gene Regulation in Sickle Cell Disease: A Randomized Phase 1 Study", PLoS Medicine, Sep. 7, 2017, Vo. 14, No. 9, e1002382, 28 Pages.
Morita M., et al., "Successful Low-Dose Leflunomide Treatment for Ganciclovir-Resistant Cytomegalovirus Infection with High-Level Antigenemia in a Kidney Transplant: A Case Report and Literature Review", Journal of Clinical Virology, Sep. 2016, vol. 82, pp. 133-138.
Newman E.M., et al., "A Phase I, Pharmacokinetic, and Pharmacodynamic Evaluation of the DNA Methyltransferase Inhibitor 5-Fuoro-2-Deoxycytidine, Administered with Tetrahydrouridine", Cancer Chemotherapy and Pharmacology, Mar. 2015, vol. 75, No. 3, 537-546, pp. 1-20.
Ng J.C.Y., et al., "Clinical Pharmacokinetic Monitoring of Leflunomide in Renal Transplant Recipients with BK Virus Reactivation: A Review of the Literature", Clinical Pharmacokinetics, Feb. 28, 2017, vol. 56, No. 9, 17 Pages.
North T.W., et al., "Tetrahydrouridine Specifically Facilitates Deoxycytidine Incorporation into Herpes Simplex Virus DNA", Journal of Virology, Mar. 1981, vol. 37, No. 3, pp. 987-993.
Ortiz-Riano E., et al., "Inhibition of Arenavirus by A3, a Pyrimidine Biosynthesis Inhibitor", Journal of Virology, Jan. 2014, vol. 88, No. 2, pp. 878-889.
Poulain F., et al., "Footprint of the Host Restriction Factors APOBEC3 on the Genome of Human Viruses", PLoS Pathogens, Aug. 14, 2020, vol. 16, No. 8, e1008718, pp. 1-30.
Riccardi R., et al., "Influence of Tetrahydrouridine on the Pharmacokinetics of Intrathecally Administered 1-beta-D-Arabinofuranosylcytosine", Cancer Research, May 1982, vol. 42, No. 5, pp. 1736-1739.
Sanjuan R., et al., "Viral Mutation Rates", Journal of Virology, Oct. 2010, vol. 84, No. 19, pp. 9733-9748.
Schat K.A., et al., "Cell-Specific Antiviral Activity of 1-(2-Fluoro-2-Deoxy-Beta-D-Arabinofuranosyl)-5-Iodocytosine (FIAC) Against Marek's Disease Herpesvirus and Turkey Herpesvirus", Antiviral Research, Oct. 1984, vol. 4, No. 5, pp. 259-270.
Schwartsmann G., et al., "DUP 785 (NSC 368390): Schedule-Dependency of Growth-Inhibitory and Antipyrimidine Effects", Biochemical Pharmacology, Sep. 1988, vol. 37, No. 17, pp. 3257-3266.
Shannon W.M., et al., "Evaluation of Carbodine, the Carbocyclic Analog of Cytidine, and Related Carbocyclic Analogs of Pyrimidine Nucleosides for Antiviral Activity Against Human Influenza Type A Viruses", Antimicrobial Agents and Chemotherapy, Dec. 1981, vol. 20, No. 6, pp. 769-776.
Shen B., et al., "Proteomic and Metabolomic Characterization of COVID-19 Patient Sera", Cell, Jul. 9, 2020, vol. 182, No. 1, pp. 59-72.e1-e5, Supplemental Figures, 30 Pages.
Simmonds P., "Rampant C-U Hypermutation in the Genomes of SARS-CoV-2 and Other Coronaviruses: Causes and Consequences for Their Short- and Long-Term Evolutionary Trajectories", mSphere, Jun. 2020, vol. 5, No. 3, e00408-20, 13 pages.
Terse P., et al., "Subchronic Oral Toxicity Study of Decitabine in Combination With Tetrahydrouridine in CD-1 Mice," International Journal of Toxicology, Mar.-Apr. 2014, vol. 33. No. 2, pp. 75-85, 22 Pages.
Totura A.L., et al., "Broad-Spectrum Coronavirus Antiviral Drug Discovery", Expert Opinion on Drug Discovery, Apr. 2019, vol. 14, No. 4, pp. 397-412.
Wong P.P., et al., "Phase I Evaluation of Tetrahydrouridine Combined With Cytosine Arabinoside", Cancer Research and Treatment, Aug. 1979, vol. 63, No. 8, pp. 1245-1249.
Xiong R., et al., "Novel and Potent Inhibitors Targeting DHODH, a Rate-Limiting Enzyme in De Novo Pyrimidine Biosynthesis, are Broad-Spectrum Antiviral Against RNA Viruses Including Newly Emerged Coronavirus SARS-CoV-2", bioRxiv, 2020, vol. 11, 983056, 31 Pages.
Zhao L., et al., "Antagonism of the Interferon-Induced OAS-RNase L Pathway by Murine Coronavirus NS2 Protein Is Required for Virus Replication and Liver Pathology", Cell Host & Microbe, Jun. 14, 2012, vol. 11, No. 6, pp. 607-616.
Zumla A., et al., "Coronaviruses—Drug Discovery and Therapeutic Options," Nature Reviews Drug Discovery, May 2016, vol. 15, No. 5, pp. 327-347.

* cited by examiner

SARS-CoV-2 Genome:

- ❑ 1/3rd (9597/29882 bp) Uridine
- ❑ 1/6th (5492/29882 bp) cytidine

SARS2 genome is 1/3rd uridine bases

A

C

B

| THU 750 mg oral dose | $AUC_{last}$ (hr*ng/ml) | $AUC_{inf}$ (hr*ng/mL) | $C_{max}$ (ng/mL) | $T_{max}$ (hr) | $T_{lag}$ (hr) | $T_{1/2}$ (hr) | $T_{last}$ (hr) | $C_{last}$ (ng/mL) |
|---|---|---|---|---|---|---|---|---|
| Number of Subjects | 15 | 15 | 15 | 15 | 15 | 15 | 15 | 15 |
| Geo. Mean | 9318 | 10298 | 1052 | 2.8 | NC | 7.2 | 24 | 90.1 |
| CV% | 30.2 | 29.3 | 32.1 | 36.5 | NC | 15.8 | 0 | 28.7 |
| Min | 5314 | 5972 | 577 | 1.5 | 0 | 5.4 | 24 | 56.4 |
| Median | 9314 | 10383 | 1000 | 2.8 | 0.25 | 7.2 | 24 | 85.2 |
| Max | 16229 | 17790 | 1950 | 4.5 | 0.25 | 10.3 | 24 | 151 |

A

B

| nCoV-2 ORF | Probability of ineffective viral replication at different C:U ratios | | | | | Expected probability of catastrophic U→C mutation after 100 cycle of replication |
|---|---|---|---|---|---|---|
| | **1.0** | **2** | **5** | **10** | **20** | |
| ORF1a | 0.01 | 0.05 | 0.1 | 0.45 | 0.6 | |
| ORF1b | 0.005 | 0.04 | 0.07 | 0.25 | 0.6 | |
| S | - | 0.01 | 0.02 | 0.1 | 0.2 | |
| ORF3a | - | 0.02 | 0.25 | 0.06 | 0.25 | |
| E | - | 0.05 | 0.3 | 0.1 | 0.4 | |
| M | - | 0.001 | 0.01 | 0.05 | 0.05 | |
| ORF6 | - | 0.1 | 0.25 | 0.3 | 0.5 | |
| ORF7a | - | 0.01 | 0.05 | 0.1 | 0.3 | |
| ORF8 | - | 0.08 | 0.09 | 0.2 | 0.5 | |
| ORF10 | - | 0.1 | 0.25 | 0.3 | 0.5 | |

TREATMENT OF RNA VIRUS INFECTION WITH A CYTIDINE DEAMINASE INHIBITOR

The present application claims priority to U.S. Provisional application Ser. No. 63/166,567, filed Mar. 26, 2021, which is herein incorporated by reference in its entirety.

FIELD OF THE INVENTION

The present invention provides compositions. systems, kits, and methods for treating a subject with an RNA virus infection (e.g., SARS-COV-2) by administering or providing a composition comprising a cytidine deaminase inhibitor (e.g., tetrahydrouridine or cedazuridine).

BACKGROUND

The Coronavirus disease 2019 (COVID-19) is an infectious disease caused by severe acute respiratory syndrome coronavirus 2 (SARS-COV-2 or SARS2). It was first identified in December 2019 in Wuhan, China, and has since spread globally, resulting in an ongoing pandemic. Common symptoms include fever, cough, fatigue, shortness of breath, and loss of smell and taste. While the majority of cases result in mild symptoms, some progress to an unusual form of acute respiratory distress syndrome (ARDS) likely precipitated by cytokine storm, multi-organ failure, septic shock, and blood clots. The time from exposure to onset of symptoms is typically around five days but may range from two to fourteen days. The virus is primarily spread between people during close contact, most often via small droplets produced by coughing, sneezing, and talking. Less commonly, people may become infected by touching a contaminated surface and then touching their face.

SUMMARY OF THE INVENTION

The present invention provides compositions, systems, kits, and methods for treating a subject with an RNA virus infection (e.g., SARS-COV-2) by administering or providing a composition comprising a cytidine deaminase inhibitor (e.g., tetrahydrouridine or cedazuridine).

In some embodiments, provided herein are methods of treating a subject infected with an RNA virus comprising: administering a composition to a subject, or providing the composition to the subject such that the subject administers the composition to themselves; wherein the subject is infected with an RNA virus; wherein the composition comprises a cytidine deaminase inhibitor.

In other embodiments, provided herein are systems, kits, and articles of manufacture comprising: a) a composition comprising a cytidine deaminase inhibitor; and b) a container selected from the group consisting of: i) an airway administration device, and ii) an orally ingestible dosage form. In some embodiments, the airway administration device is a nebulizer. In further embodiments, the orally ingestible dosage form is a capsule or pill that comprises an enteric coating.

In further embodiments, provided herein are compositions comprising: a) a cytidine deaminase inhibitor; and b) an inhibitor of pyrimidine synthesis.

In additional embodiments, provided herein are in vitro compositions comprising: a) a cytidine deaminase inhibitor drug: and b) an inhibitor of pyrimidine synthesis.

In some embodiments, provided herein are systems or kits comprising: a) a composition comprising a cytidine deaminase inhibitor drugs: and b) instructions for treating a subject with the composition, wherein the subject is infected with: an RNA virus.

In other embodiments, provided herein are articles of manufacture comprising an orally ingestible pill or capsule, wherein the orally ingestible pill or capsule comprises: a) a composition comprising a cytidine deaminase inhibitor; and b) an enteric coating which surrounds the composition. In some embodiments, the pill or capsule comprises a capsule, wherein the capsule comprises a softgel. In additional embodiments, the softgel comprises gelatin.

In certain embodiments, the cytidine deaminase inhibitor comprises tetrahydrouridine, cedazuridine, and/or diazepinone riboside. In other embodiments, the cytidine deaminase inhibitor comprises a compound of Formula I, wherein Formula I is as follows:

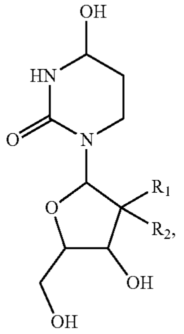

or a pharmaceutically acceptable salt of the compound, wherein:

$R_1$ and $R_2$ are independently selected from the group consisting of hydrogen, halo, cyano, nitro, sulfhydryl, hydroxyl, formyl, carboxyl, COO ($C_1$ to $C_6$ straight or branched chain alkyl), COO ($C_1$ to $C_6$ straight or branched chain alkenyl), COO ($C_1$ to $C_6$ straight or branched chain alkynyl), CO ($C_1$ to $C_6$ straight or branched chain alkyl), CO ($C_1$ to $C_6$ straight or branched chain alkenyl), CO ($C_1$ to $C_6$ straight or branched chain alkynyl), $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy: wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy, may be independently unsubstituted or substituted with one to four substituents independently selected from the group consisting of halo, hydroxyl, cyano, nitro, formyl, carboxyl, and sulfhydryl;

and provided that when one of $R_1$ and $R_2$ is —H, then the other is not —H, —OH or —$CH_2OH$.

In certain embodiments, the RNA virus is $SAR_2$-COV-2. In other embodiments, the subject is further administered a pyrimidine synthesis inhibitor. In additional embodiments, the pyrimidine synthesis inhibitor comprises teriflunomide. In some embodiments, the pyrimidine synthesis inhibitor comprises leflunomide. In additional embodiments, the subject is a human. In other embodiments, the subject is an animal (e.g., a dog, cat, horse, cow. pig, or other livestock).

In other embodiments, the subject is further administered an inhibitor of viral RNA polymerase. In additional embodiments, the viral RNA polymerase inhibitor comprises remdesivir. In additional embodiments, the subject is a human. In other embodiments, the subject is an animal (e.g., a dog, cat, horse, cow, pig, or other livestock). In further embodiments, the administering is such that the subject receives about 5-100 mg of the cytidine deaminase inhibitor per kilogram of the subject per day (e.g., for 5-7 consecutive days). In other embodiments. the administering is intravenous administration or via the subject's airway. In further embodiments, the subject administers the composition to themselves (e.g., orally). In additional embodiments, the composition is provided to the subject in oral dosage form (e.g., the subject administers the composition to themselves orally), and wherein the composition comprises a pill or capsule. In particular embodiments, the subject receives about 5-100 mg of the cytidine deaminase inhibitor per kilogram of the subject per day.

In additional embodiments, the methods further comprise: administering or providing an anti-coagulant to the subject. In other embodiments, the methods further comprise: administering or providing a different anti-viral agent to the subject. In additional embodiments, the subject is on a ventilator. In particular embodiments, the composition further comprises a physiologically tolerable buffer.

DESCRIPTION OF THE FIGURES

FIG. 9 calculation by: P(s)=(1−P(L))[(λ exp−λs)/1−e−λ) if 0<s<1; P(s)=P(L) if s=1 and P(s)=0) otherwise si=1−ai/a0)ai and a0 are growth rates of mutant and reference viruses respectively. Estimates of distribution of fitness effects of random single-nucleotide (U→C) substitutions is based on experimental data (Site-directed mutagenesis—Sanjua'n R et al., J. Virol. 2010: 9733-9748). Calculations in R-studio.

DETAILED DESCRIPTION

Figure 1:
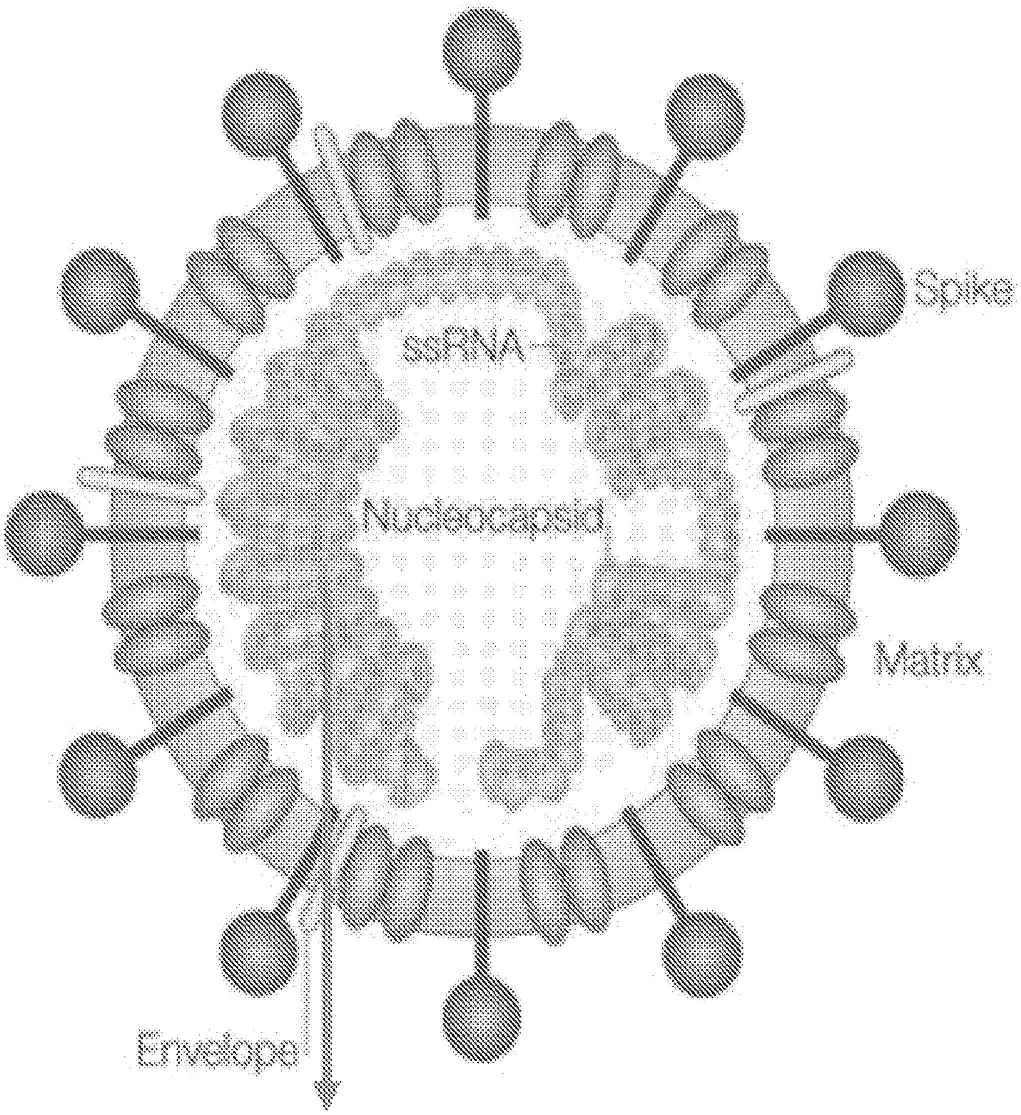
FIG. 1 shows an schematic of $SAR_2$, which shows the SARS2 genome is ⅓rd uridine bases.

The present invention provides compositions, systems, kits, and methods for treating a subject with an RNA virus infection (e.g., SARS-COV-2) by administering or providing a composition comprising a cytidine deaminase inhibitor (e.g., tetrahydrouridine or cedazuridine).

Viruses absolutely depend on host cell supplies of nucleotides to replicate. For example, SARS-COV-2 (SARS2) that causes Corona Virus Disease 2019 (COVID-19), requires massive amounts of host cell uridine—⅓rd of its genome is uridine (9597/29882 bp) in contrast to ⅙th cytidine (5492/29882). Uridine is moreover required for sub-genome positive strand RNA synthesis/viral function. The human pyrimidine metabolism salvage enzyme cytidine deaminase (CDA) facilitates these SARS2 uridine demands by systemically and rapidly deaminating cytidines into uridine. The CDA inhibitor tetrahydrouridine (THU), therefore, reduces uridine available for systemic salvage by up to 90%, at standard, non-toxic doses. In addition to starving SARS2 of uridines needed to replicate. lower uridine:cytidine ratio is likely to increase errors by low fidelity SARS2 RNA polymerase. Importantly, THU has proven safe in clinical trials, presumably because of the high fidelity of human RNA polymerase and because THU does not imbalance deoxynucleotides.

THU has a number of advantages for treatment of RNA viral infection. For example, (i) THU decreases uridine in non-dividing host cells, the target cells of SARS2 and many other viruses: (ii) THU has established clinical safety, is not cytotoxic, and spares host immunity needed for long-term viral suppression and herd immunity: (iii) the proposed, non-limiting mechanism suggests pan-coronavirus anti-viral activity: (iv) THU can be delivered orally, and is practical and cost-effective for out-patient, post-exposure and worldwide use, and (v) augments inhibitors of viral polymerase without adding toxicity, In sum, THU to inhibit CDA may be used to meaningfully treat COVID-19, future pandemics (e.g., not yet known RNA viruses), and even non-pandemic viral disease.

While understanding the mechanism is not necessary to practice the invention, and the invention is not limited to any particular mechanism, is proposed that administration of THU (or other cytidine deaminase inhibitor) can be used to impede/increase errors in viral replication without suppressing host immunity and thus attenuate disease long enough for effective host immune response. Also, in certain embodiments, THU (or other cytidine deaminase inhibitor) is beneficially provided in combination with inhibitors of de novo pyrimidine synthesis since THU enables their dose- and/or duration-reduction to moderate immune-suppressing side-effects yet may more profoundly starve virus of uridine. In certain embodiments, THU or other cytidine deaminase inhibitor is employed (e.g., via oral administration) to treat RNA viruses, such as SARS2, future pandemics (not yet known RNA viruses), and even non-pandemic viral disease. THU is non-cytotoxic, and crucially spares immunity needed for long-term viral suppression and herd-immunity.

Examples of RNA viruses treated with the methods provided herein include, but are not limited to, Orthomyxoviruses, Hepatitis C Virus (HCV), Ebola disease, SARS, SARS2, influenza, polio measles and retrovirus including adult Human T-cell lymphotropic virus type I (HTLV-1) human immunodeficiency virus (HIV), the common cold, influenza, MERS, COVID-19, Dengue Virus, hepatitis C, hepatitis E, West Nile fever virus, rabies virus, polio virus, mumps virus, and measles virus. In particular embodiments, the enveloped virus is a SARS-COV-2 variant selected from B.1.351 ("South African Variant) or B.1.1.7 ("UK variant") or "delta" or "omicron."

In certain embodiments, the pharmaceutical formulations containing the cytidine deaminase inhibitor are administered orally, in the form of a pill capsule, gel-cap, or the like. In some embodiments, the oral administration is 5-100 mg of the cytidine deaminase inhibitor (e.g., THU) per kilogram of subject (e.g.,. 5 . . . 10 . . . 20 . . . 30 . . . 40 . . . 50 . . . 75 . . . 100 mg/kg). In certain embodiments, provided herein a pill or capsule containing a cytidine deaminase inhibitor (e.g., tetrahydrouridine).

The cytidine deaminase inhibitor may be formulated in pharmaceutical formulation and/or medicament. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. In certain embodiments, the cytidine deaminase inhibitor is mixed with a buffer (e.g., phosphate buffered saline).

The cytidine deaminase inhibitor may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9)-lauryl ether, glycocholate and deoxycholate. Aqueous and nonaqueous aerosols are typically used for delivery of THU by inhalation.

Ordinarily, an aqueous aerosol is made by formulating an aqueous solution or suspension of the cytidine deaminase inhibitor (e.g., tetrahydrouridine) together with conventional pharmaceutically acceptable carriers and stabilizers. The carriers and stabilizers vary with the requirements of the particular compound, but typically include nonionic surfactants (e.g., TWEENs. Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver the cytidine deaminase inhibitor (e.g., tetrahydrouridine).

Aerosols containing a cytidine deaminase inhibitor for use according to the present invention are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example. gelatin for use in an inhaler or insufflator may be formulated containing a powder mix of a cy tidine deaminase inhibitor and a suitable powder base such as lactose or starch. Delivery of aerosols of the present invention using sonic nebulizers is advantageous because nebulizers minimize exposure of the agent to shear, which can result in degradation of the compound.

For nasal administration, the pharmaceutical formulations and medicaments with a cytidine deaminase inhibitor may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the cytidine deaminase inhibitor may be formulated in oily solutions or as a gel. For administration of nasal aerosol, any suitable propellant may be used including compressed air, nitrogen, carbon dioxide, or a hydrocarbon based low boiling solvent.

Dosage forms for the topical (including buccal and sublingual) or transdermal or oral administration of a cytidine deaminase inhibitor of the invention include powders, sprays, pills, gel-caps, ointments, pastes, creams, lotions, gels, solutions, and patches. A cytidine deaminase inhibitor may be mixed under sterile conditions with a pharmaceutically-acceptable carrier or excipient, and with any preservatives, or buffers, which may be required. Powders and sprays can be prepared, for example, with excipients such as lactose. talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In certain embodiments, the pill or capsule herein comprises a gelatin encapsulated dosage form (e.g., a softgel). In certain embodiments, the gelatin encapsulation of a deaminase inhibitor is composed of gelatin, glycerin, water, and optionally caramel. In particular embodiments, the pills and capsules herein are coated with an enteric coating (e.g., to avoid the acid environment of the stomach, and release most of the cytidine deaminase inhibitor in the small intestines of a subject). In some embodiments, the enteric coating comprises a polymer barrier that prevents its dissolution or disintegration in the gastric environment, thus allowing the cytidine deaminase inhibitor herein to reach the small intestines. Examples of enteric coatings include, but are not limited to, Methyl acrylate-methacrylic acid copolymers: Cellulose acetate phthalate (CAP): Cellulose acetate succinate: Hydroxypropyl methyl cellulose phthalate: Hydroxypropyl methyl cellulose acetate succinate (hypromellose acetate succinate): Polyvinyl acetate phthalate (PVAP): Methyl methacrylate-methacrylic acid copolymers: Shellac: Cellulose acetate trimellitate: Sodium alginate: Zein: COLORCON, and an enteric coating aqueous solution (ethylcellulose, medium chain triglycerides [coconut], oleic acid, sodium alginate, stearic acid) (e.g., coated softgels). Additional enteric coatings are described in Hussan et al., IOSR Journal of Pharmacy, e-ISSN: 2250-3013, p-ISSN: 2319-4219, Volume 2 Issue 6, November-December 2012, PP.05-11, herein incorporated by references in its entirety, and particularly for its description of enteric coatings.

Transdermal patches have the added advantage of providing controlled delivery of the cytidine deaminase inhibitor to the body. Such dosage forms can be made by dissolving or dispersing the cytidine deaminase inhibitor in the proper medium. Absorption enhancers can also be used to increase the flux of the cytidine deaminase inhibitor (e.g., THU) across the skin. The rate of such flux can be controlled by either providing a rate controlling membrane or dispersing the compound in a polymer matrix or gel.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Specific dosages of the cytidine deaminase inhibitor be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

In particular embodiments, courses of treatment can be administered concurrently to a subject, i.e., individual doses of the cytidine deaminase inhibitor herein and secondary therapeutic (e.g., pyrimidine synthesis inhibitor) are administered separately yet within a time interval such that cytidine deaminase inhibitor can work together with the additional therapeutic agent. For example, one component can be administered once per day, twice per day or three times per day in combination with the other components that can be administered once or twice or thrice in a week. In other words, the dosing regimens are carried out concurrently even if the therapeutics are not administered simultaneously or during the same day.

EXAMPLE

Example 1

Tetrahydrouridine for COVID-19 Treatment

There is urgent need for a definitive COVID-19 therapeutic that is orally administered and safe enough for wide-spread use. COVID-19 is a world-wide emergency. There are currently no approved definitive oral anti-virals to treat COVID-19 (e.g., the adenosine analog remdesivir is intravenously administered to hospitalized patients). This Example shows that THU is a candidate to fulfil this need.

Figure 2:
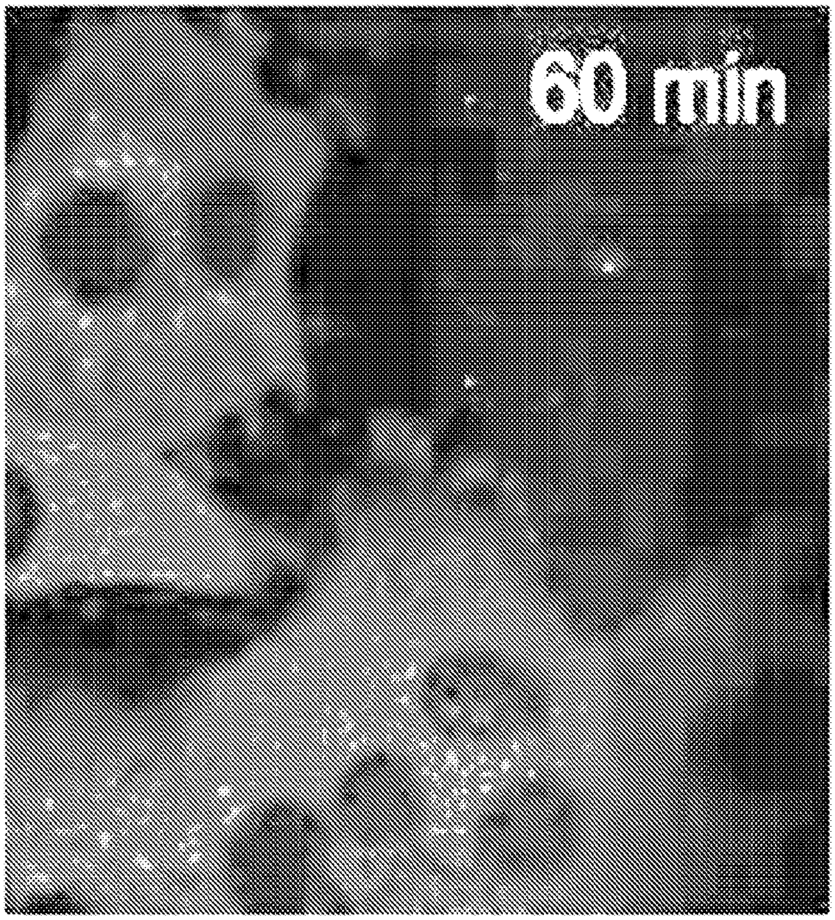
FIG. 2 shows the uridine (U) demands of coronavirus visualized (U incorporation into perinuclear coronaviral RNA)2. $LR_7$ cells infected with MHV coronavirus (95% similar to SARS2) fed with labelled uridine (ethnyl-uridine) for 1 hr (data from Hagemeijer et al., Visualizing coronavirus RNA synthesis in time by using click chemistry. *J Virol.* 2012:86(10):5808-5816).
Figure 3:
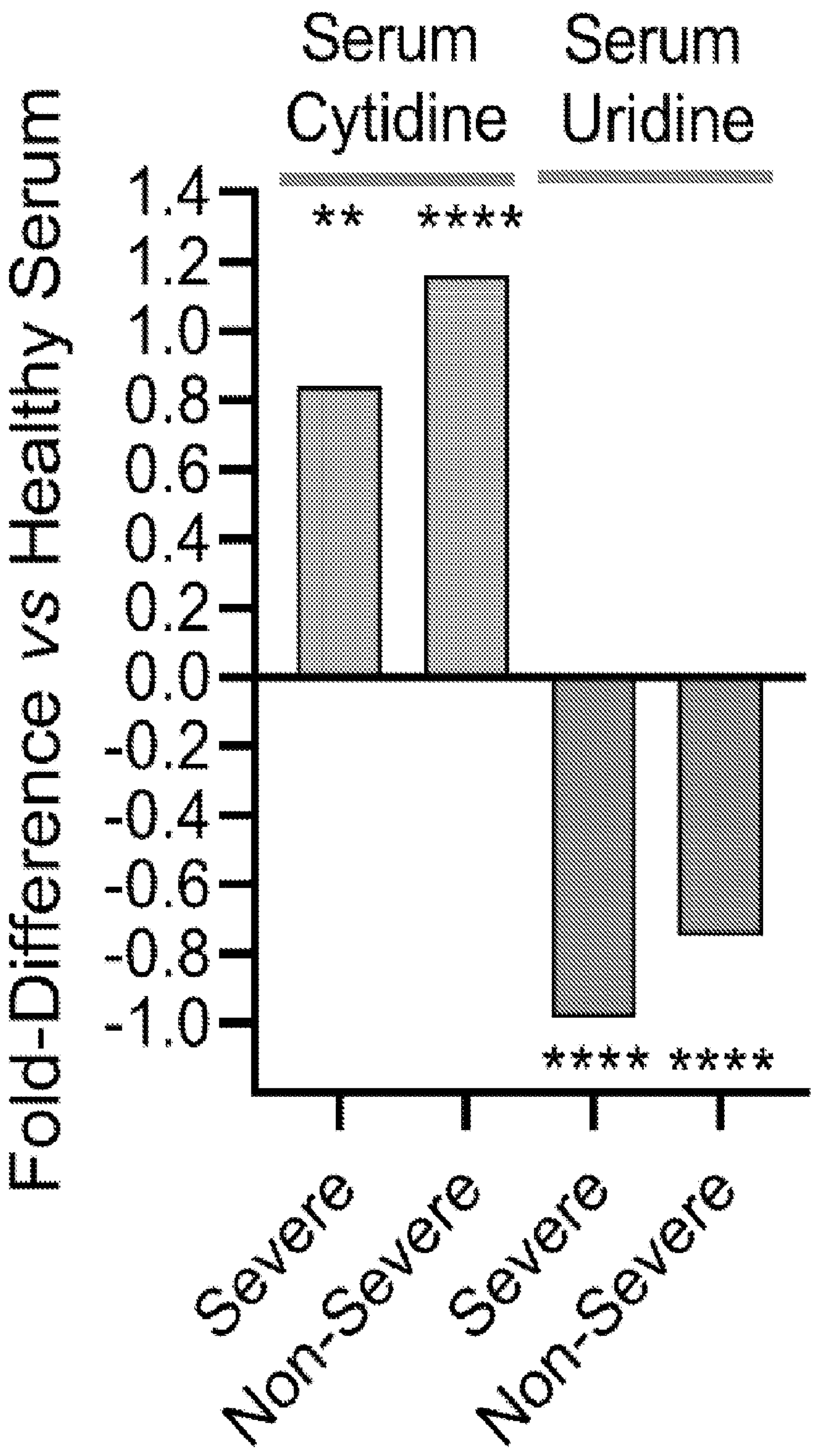
FIG. 3 shows that serum of patients with COVID19 is substantially depleted of uridine, even as cytidine is simultaneously increased.
Figure 4:
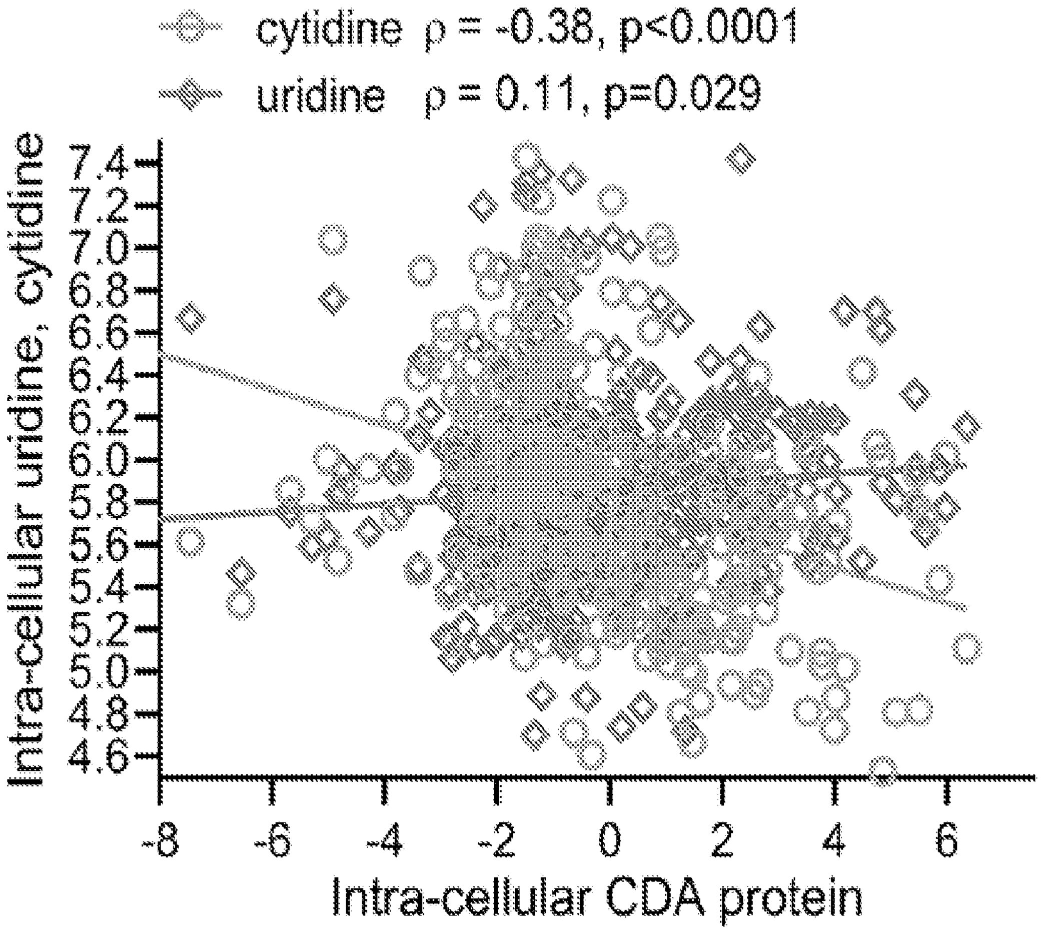
FIG. 4 shows CDA deaminates cytidine to maintain uridine levels—shown is the negative correlation between intra-cellular CDA protein and cytidine, that stabilizes cellular uridine amounts (analyses of 370 cancer cell lines—Cancer Cell Line Encyclopedia): p-values Spearman correlation coefficients, 2-sided.
Figure 5:
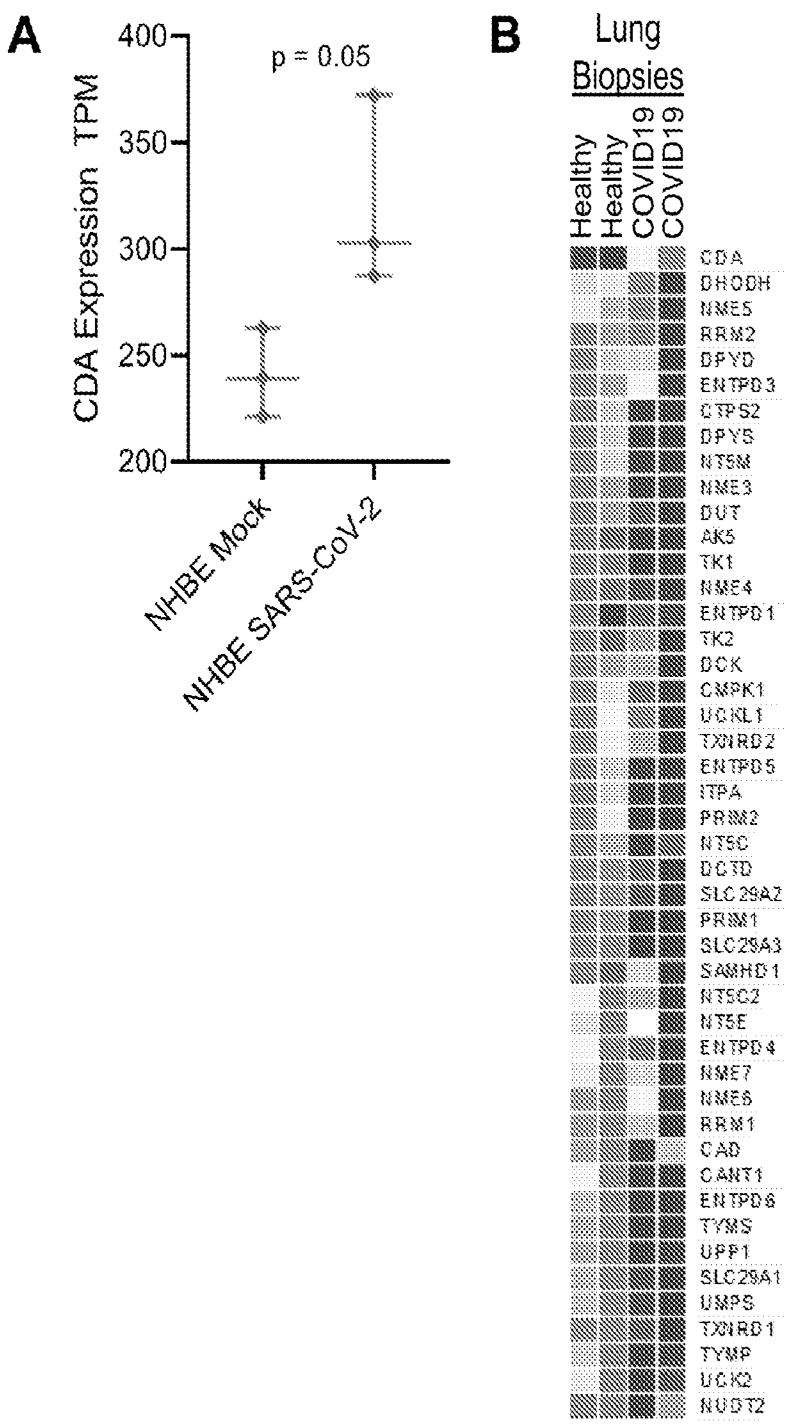
FIG. 5 shows A) CDA is upregulated in normal human bronchial epithelium (NHBE) infected with SARS2 vs mock-infected cells. Gene expression by RNA-seq TPM=transcripts per million—GSE147507. B) CDA is the single most upregulated pyrimidine metabolism enzyme in human bronchial epithelial tissue biopsies from Covid19 vs non-Covid19 controls—RNA seq GSE147507. All known pyrimidine salvage and de novo enzymes.

SARS2 requires massive amounts of host cell uridine to replicate, and the enzyme CDA supplies these needs. Viral replication absolutely depends on nucleotides hijacked from host cells: in particular, SARS2 requires massive amounts of host cell uridine to replicate and cause disease—⅓rd of its genome (9597/29882 bp) is uridine in contrast to ⅙th (5492/29882) cytidine (FIG. 1, 2) (FIG. 2 data from Hagemeijer et al., Visualizing coronavirus RNA synthesis in time by using click chemistry. *J Virol.* 2012:86(10):5808-5816). Uridine is moreover required for sub-genome positive strand RNA synthesis and viral function (2). Accordingly, the serum of patients with COVID-19 is depleted of uridine (FIG. 3). Human cytidine deaminase (CDA) is a pyrimidine metabolism enzyme that facilitates these high uridine demands by rapidly and systemically deaminating cytidines into uridine— CDA maintains uridine levels, as a physiologic priority, at the expense of cytidine levels (FIG. 4). Therefore, consistent with, and expected from, the systemic depletion of uridine caused by SARS2 infection (FIG. 3). CDA is the pyrimidine metabolism enzyme singularly upregulated in bronchial biopsies of COVID-19 patients, and is also upregulated in bronchial epithelial cells infected by SARS2 in vitro (FIG. 5).

THU is a safe and potent inhibitor of CDA. THU is a potent, reversible inhibitor of CDA, with Ki~10−7 M, and $IC_{50\sim0.34}$ μM, via reversible binding to each sub-unit of the CDA homotetramer (7).

Figure 6:
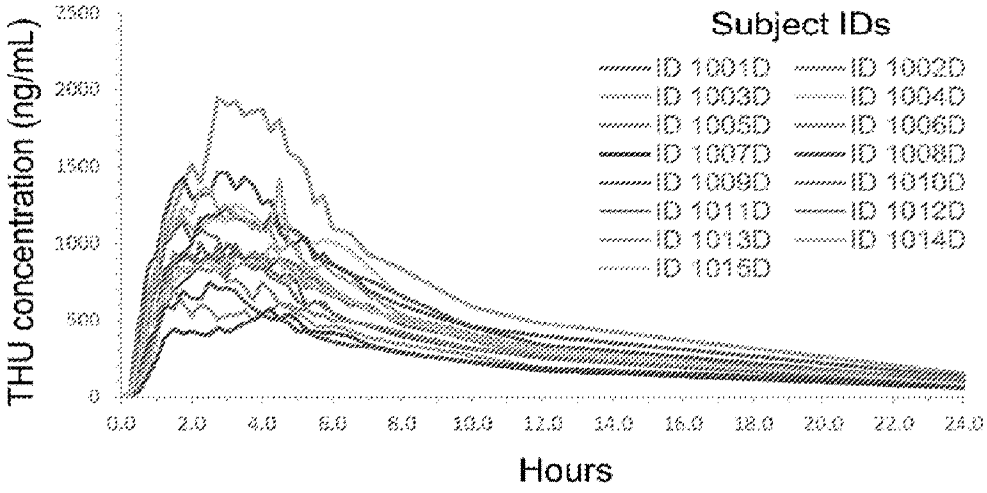
FIG. 6 shows pharmacokinetics (PK) of THU 750 mg (~10 mg/kg), ingested as three immediate-release capsules containing 250 mg of THU/capsule, in 15 healthy human male subjects—we then extended these results to an additional 22 females and 24 males (NCT04086238). A) Concentration-time profiles. The $IC_{50}$ of THU for CDA is ~0.3 uM, corresponding to a THU concentration of ~74 ng/mL. B) THU PK summary statistics. C) THU AUCinf inversely correlated with body weight.
Figure 6:
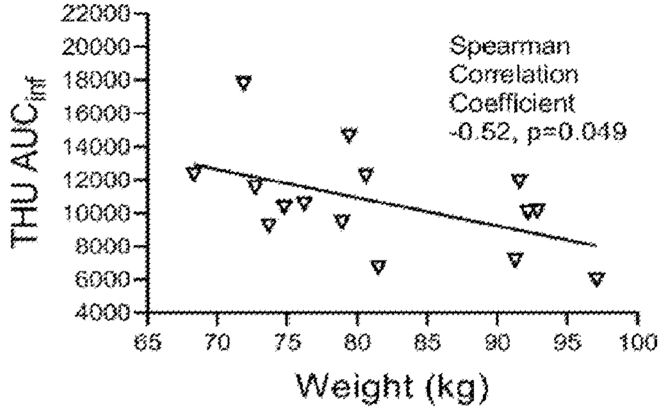

THU clinical pharmacokinetics. THU alone at a fixed dose of 750 mg, ingested orally as three immediate-release capsules containing THU 250 mg/capsule, in 15 healthy male human volunteers with body weights between 60-100 kg, produced THU Cmax of 2-8 uM (500-2000 ng/mL) (FIG. 6A, B). These concentrations are comfortably above the $IC_{50}$ (0.3 uM) for inhibition of CDA (35). Tmax was achieved at ~3 hours after administration (FIG. 6A, B). The variation in THU Cmax and AUCinf observed in this study correlated with body weight (FIG. 6C). We went on to evaluate THU pharmacokinetics in an additional 22 females and 24 males in fasted as well as fed states, recapitulating these results (NCT04086238). The main pathway of excretion is through the kidneys with approximately 50% of the administered drug excreted within 24 h and 100% elimination within 48 hours (36).

Figure 7:
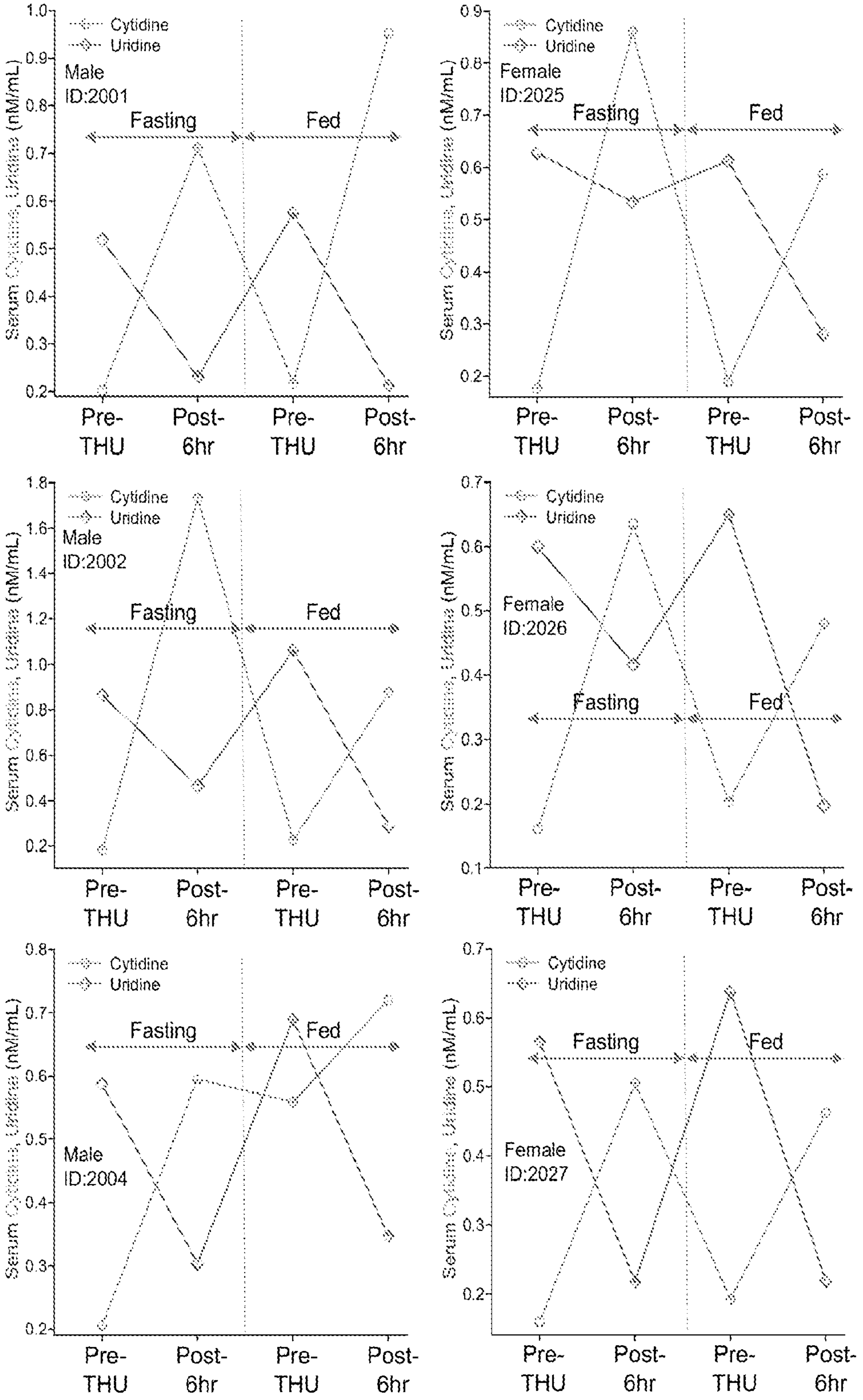
FIG. 7 shows single THU exposures decreased serum uridine levels by >50-80%. Volunteers (3 males; 3 females) received a single THU dose of 750 mg 7 days apart, the 1st dose in a fasted state and the 2nd after a standard FDA meal.

THU clinical pharmacodynamics. We have evaluated the clinical pharmacodynamics of THU by measuring the effect of standard clinical doses (FIG. 7) on serum uridine levels. A single THU dose of 750 mg decreased serum uridine levels by 50-90% in both the fasted and fed states, in both males and females, simultaneously increasing serum cytidine levels (that is, inverting the usual systemic uridine: cytidine ratio) (FIG. 7). We and others have also measured THU clinical pharmacodynamics via its effects on deamination of co-administered cytidine analogs, and found an ~90% reduction in cytidine analog deamination (4,5,37,38).

THU clinical safety. Although THU is not an approved drug, it has been extensively evaluated in several Phase 1 and 2 clinical trials (hematology and oncology clinical trials) by our group and by the National Cancer Institute. These several clinical evaluations, and extensive IND pre-clinical animal studies, have established excellent safety at doses that are pharmacodynamically highly active in inhibiting CDA (36-44), and for durations of administration exceeding 1 year (summarized in Table 1).

TABLE 1

Completed and ongoing clinical trials with tetrahydrouridine (THU)

| | THU Dose/Day (mpk = mg/kg) | Total THU Dose/day (BSA = 1.62 $m^2$; Weight 60 kg) | THU Schedule | Duration of Admin. | Total dose over duration of trial | Route | Number of Patients | $2^{nd}$ Drug (combined with) | Ref |
|---|---|---|---|---|---|---|---|---|---|
| 1 | 200 $mg/m^2$ (5.5 mpk) | 324 mg | | Single dose | | IV, SQ, PO | 5 | None | 24 |
| 2 | 10-50 mpk | 600-3000 mg | Daily for 23 d | 23 days | Up to ~60,000 mg | IV | 4 | None | 19 |
| 3 | 50 mpk | 3000 mg | | Single dose | | IV, PO | 4 | None | 25 |
| 4 | 10-50 mpk | 600-3000 mg | | Single dose | | IV | 2 | IV Ara-C 0.003 mpk | 25 |
| 5 | 350 $mg/m^2$ (9.5 mpk) | 567 mg | | Single dose | | IV | 7 | IV 5-fluoro-2'-deoxycytidine (5-FdC) 100 $mg/m^2$ | 16 |
| 6 | 1750 $mg/m^2$ (47 mpk) | 2835 mg | | Single dose | | PO | 7 | PO 5-FdC 100 $mg/m^2$ | 16 |
| 7 | 350 $mg/m^2$ (9.5 mpk) | 567 mg | Daily for 10 d every 28 d | Up to 10 months | ~56,700 mg | IV | 95 | IV 5-FdC 100 $mg/m^2$ | 33 |
| 8 | 2-4 mpk | 120-240 mg | Daily for 3 d every wk | >1 Year | >42,000 mg | PO | 2 | Oral 5-Azacytidine 0.2 mpk/d for 3 d every wk | 23 |
| 9 | 700 $mg/m^2$ (19 mpk) | 1134 mg | 350 $mg/m^2$ every 12 h for 4 d | 4 days | ~4536 mg | IV | 32 | IV Ara-C 100-200 $mg/m^2$ every 12 h × 4 d | 22 |
| 10 | 350 $mg/m^2$ (9.5 mpk) | 567 mg | Daily for 5 d | 5 days | ~2835 mg | IV | 11 | IV 5-FdC 5-80 $mg/m^2$/d for 5 d | 11, 34 |
| 11 | 700 $mg/m^2$ (19 mpk) | 1134 mg | 350 $mg/m^2$ every 12 h for 4 d | 3-4 days | ~4536 mg | IV | 8 | IV Ara-C 200 $mg/m^2$ every 12 h × 4 d & carboplatin 900 $mg/m^2$ total dose | 17 |
| 12 | 25-50 mpk | 1500-3000 mg | Daily for 5-7 d every 28 d | 7 months | >120,000 mg | IV | 46 | IV Ara-C 0.1-0.2 mpk/d × 5-7 d | 19 |
| 13 | 350 $mg/m^2$ (9.5 mpk) | 567 mg | Daily for 5-10 d every 21-28 d | >1 year | >85,000 mg | IV | 58 | IV 5-FdC 2.5-180 $mg/m^2$/d for 5 d every 21 d OR for 5 d in each of 2 consecutive wks every 28 d | 35 |
| 14 | ~10 mpk | 500-1000 mg | 2X/wk | >1 year | 120,000 mg | PO | 7 | Decitabine ~0.2 mpk | 24, 36 |
| 15 | ~10 mpk | 500-1,000 mg | Daily x 5 d/wk for 2 wks then 2X/wk | 12 weeks | 20,000 mg | PO | 13 | Decitabine ~0.2 mpk | 35, 37 |
| 16 | ~10 mpk | 750 mg | 1X/wk for 4 wk | 4 weeks | 3000 mg | PO | 16 | Decitabine ~0.2 mpk | NCT03828084 |
| 17 | ~10 mpk | 750 mg | 1X/wk for 4 wk | 4 weeks | 3000 mg | PO | 46 | Decitabine ~0.2 mpk | NCT04086238 |
| 18 | ~10 mpk | 500-1250 mg | 2X/wk for 2 of every 3 wk | 9 weeks | Study in progress | PO | 85 | Decitabine & Pembrolizumab | NCT03233724 |
| 19 | ~10 mpk | 500-1000 mg | 1X/wk for >24 wk | 2X/wk for >24 weeks | Study in progress | PO | 20 | Decitabine | NCT04055818 |
| 20 | 3000 mg (~50 mpk) | 3000 mg | Daily for 6 d every 21 d | Study in progress | | PO | 59 | 5-FdC | NCT01534598 |
| 21 | ~10 mpk | 600 mg | 2X/wk | >1 year | 90,000 mg | PO | 13 | Nivolumab & Decitabine | NCT02664181 |
| 22 | 720 $mg/m^2$ (19.5 mpk) | 1166 mg | Daily for 13 d every 21 d | | >15,000 mg | IV | 2 | Cytochlor & Radiation | NCT00521183 |
| 23 | 350 $mg/m^2$; 3,000 mg (~50 mpk) | 567-3000 mg | | Single dose | | IV, PO | | 5-FdC | NCT01479348 |
| 24 | 350 $mg/m^2$ (9.5 mpk) | 567 mg | Daily for 10 d every 21 d | Study in progress | | IV | 25 | 5-FdC | NCT01041443 |
| 25 | 350 $mg/m^2$ (9.5 mpk) | 567 mg | Daily x 5 d/wk for 2 wk | 2 weeks | 6,000 mg | IV | 95 | 5-FdC | NCT00978250 |

TABLE 1-continued

Completed and ongoing clinical trials with tetrahydrouridine (THU)

| | THU Dose/Day (mpk = mg/kg) | Total THU Dose/day (BSA = 1.62 $m^2$; Weight 60 kg) | THU Schedule | Duration of Admin. | Total dose over duration of trial | Route | Number of Patients | $2^{nd}$ Drug (combined with) | Ref |
|---|---|---|---|---|---|---|---|---|---|
| 26 | 350 mg/$m^2$ (9.5 mpk) | ~700 mg | Daily x 5 d/wk for 2 wk | 9 days | | IV | 58 | 5-FdC | NCT00359606 |
| 27 | 720 mg/$m^2$ (19.5 mpk) | 1166 mg | Daily for 13 d every 21 d | | >15,000 mg | IV | 1 | Cytochlor & Cisplatin | NCT00077051 |

Figure 8:
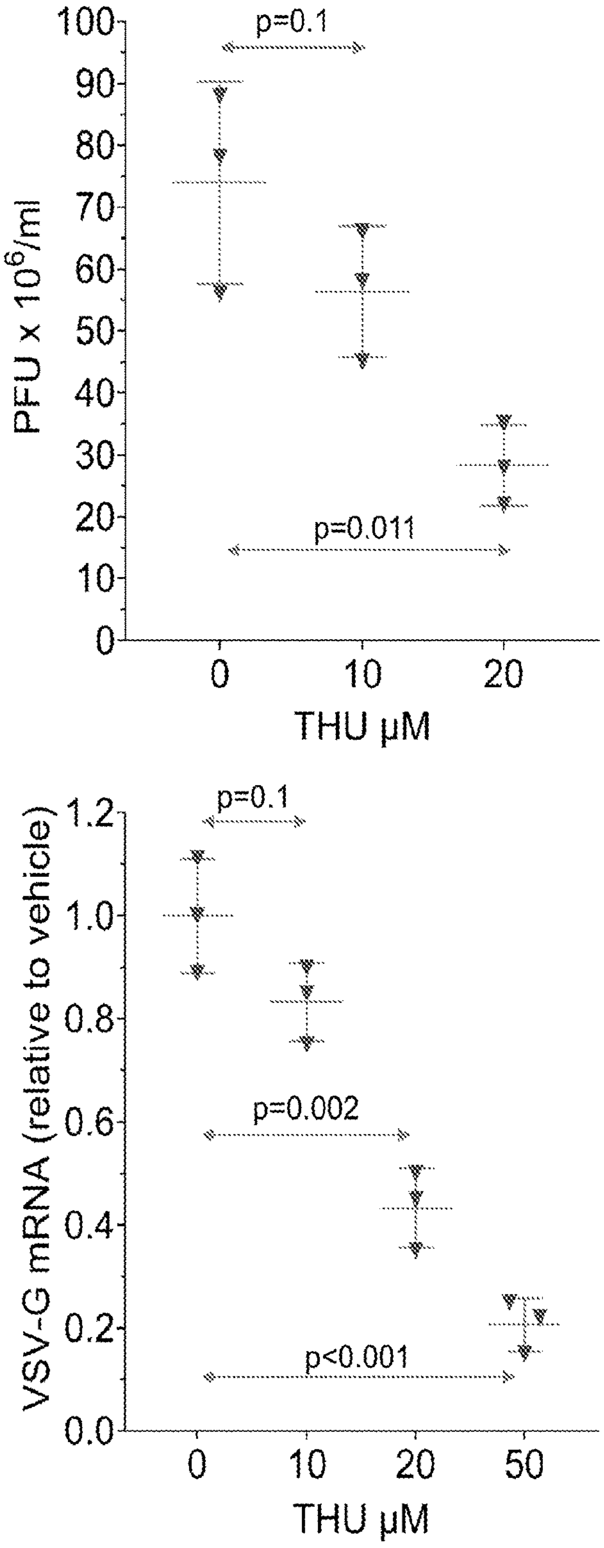
FIG. 8 shows THU inhibited coronavirus replication in vitro. Normal lung epithelial cells at 60% confluence were infected with 5 pfu/ml VSV (gift of Amiya Banerjee) for 1 hour at 37 0C. THU treatment for 24 hours. For plaque assays, the supernatant were used in indicator cell line BHK21. mRNA was measured by QRT-PCR. Mean±SD. p-value t-test 2-sided.

THU inhibits coronavirus replication in vitro. We evaluated the effects of THU as a single agent on coronavirus replication in vitro. THU at clinically relevant concentrations significantly inhibited coronavirus (VSV) replication in human lung epithelial cells, measured by plaque assays and by QRT-PCR (FIG. 8).

Figure 9:
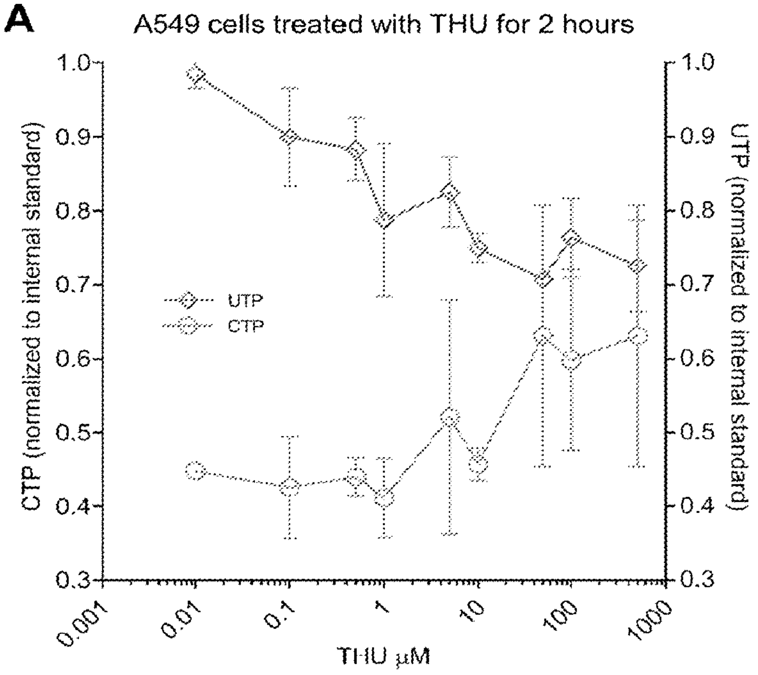
FIG. 9 shows THU mediated increase in C:U and CTP:UTP ratio is predicted to increase U→C errors in the viral genome. A) Effects of 2 hours of THU on UTP and CTP levels in A549 lung cancer cells. Nucleotide levels by LCMS/MS. B) Probabilities of ineffective viral replication at different C:U ratios.

Decreasing the uridine:cytidine ratio is also expected to increase errors in viral replication that promote immune-recognition. Serial sequencing of SARS2 during the pandemic has demonstrated progressive C→U mutations, attributed to selection for evasion of host $APOBEC_3$ anti-viral editing (6,45). THU changes uridine:cytidine and UTP:CTP stoichiometry such that error-prone viral RNA polymerase is more likely to execute U→C mutations, that will reintroduce vulnerability to $APOBEC_3$ anti-viral editing and innate immunity response (6,45) (FIG. 9A, B).

Figure 10:
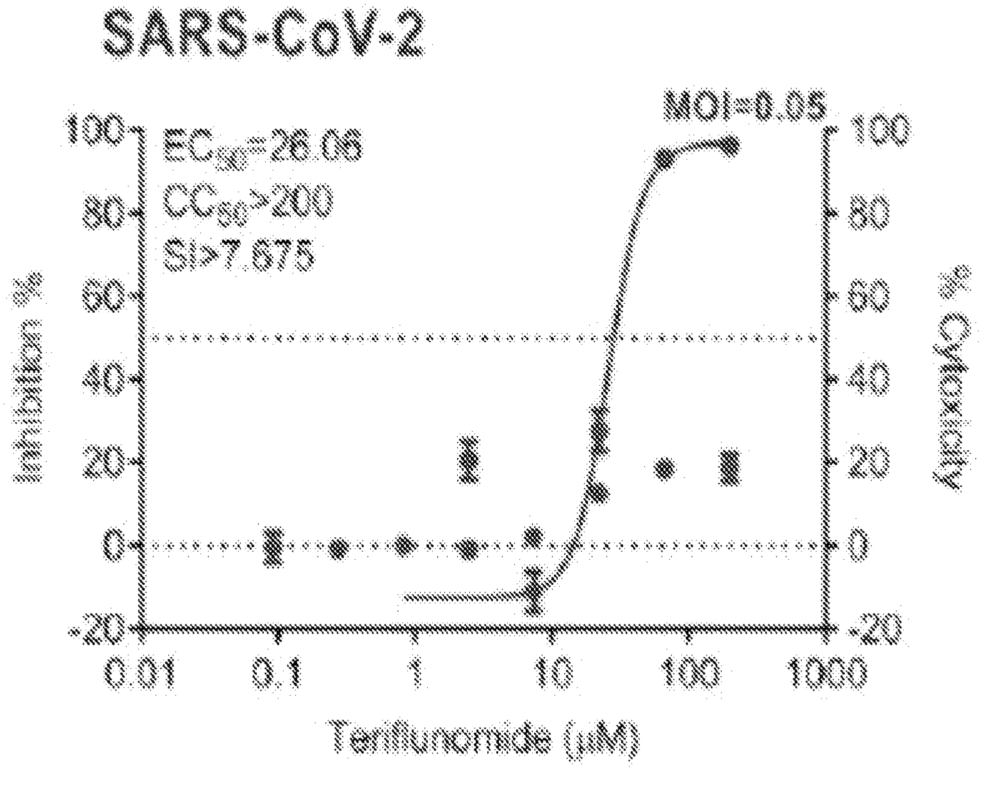
FIG. 10 shows Teriflunomide at clinically relevant concentrations (routine Cmax is 10-100 uM) potently inhibits SARS2 replication (red) with minimal host cell cytotoxicity (green). Xiong R et al, BioRXiv 2020 (data from Xiong, et al. (2020). Novel and Potent Inhibitors Targeting DHODH, a Rate-Limiting Enzyme in De Novo Pyrinndine Biosynthesis, Are Broad-Spectrum Antiviral against RNA Viruses Including Newly Emerged Coronavirus SARS-CoV-2. bioRxiv 11, 983056).
Figure 11:
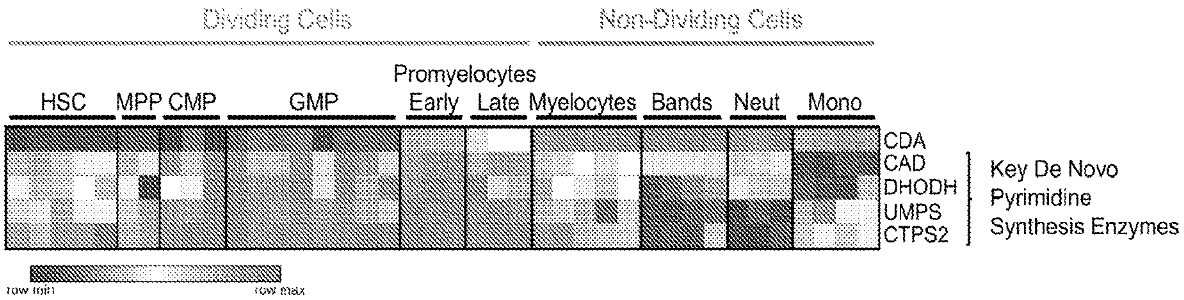
FIG. 11 shows dividing cells heavily utilize de novo pyrimidine synthesis (CAD, DHODH, UMPS, CTPS2), which is downregulated simultaneous with CDA upregulation, during the transition to non-dividing terminally-differentiated states. Shown is gene expression in during normal hematopoiesis from stem cells to terminally-differentiated granulocytes (microarray gene expression, BloodSpot).
Figure 12:
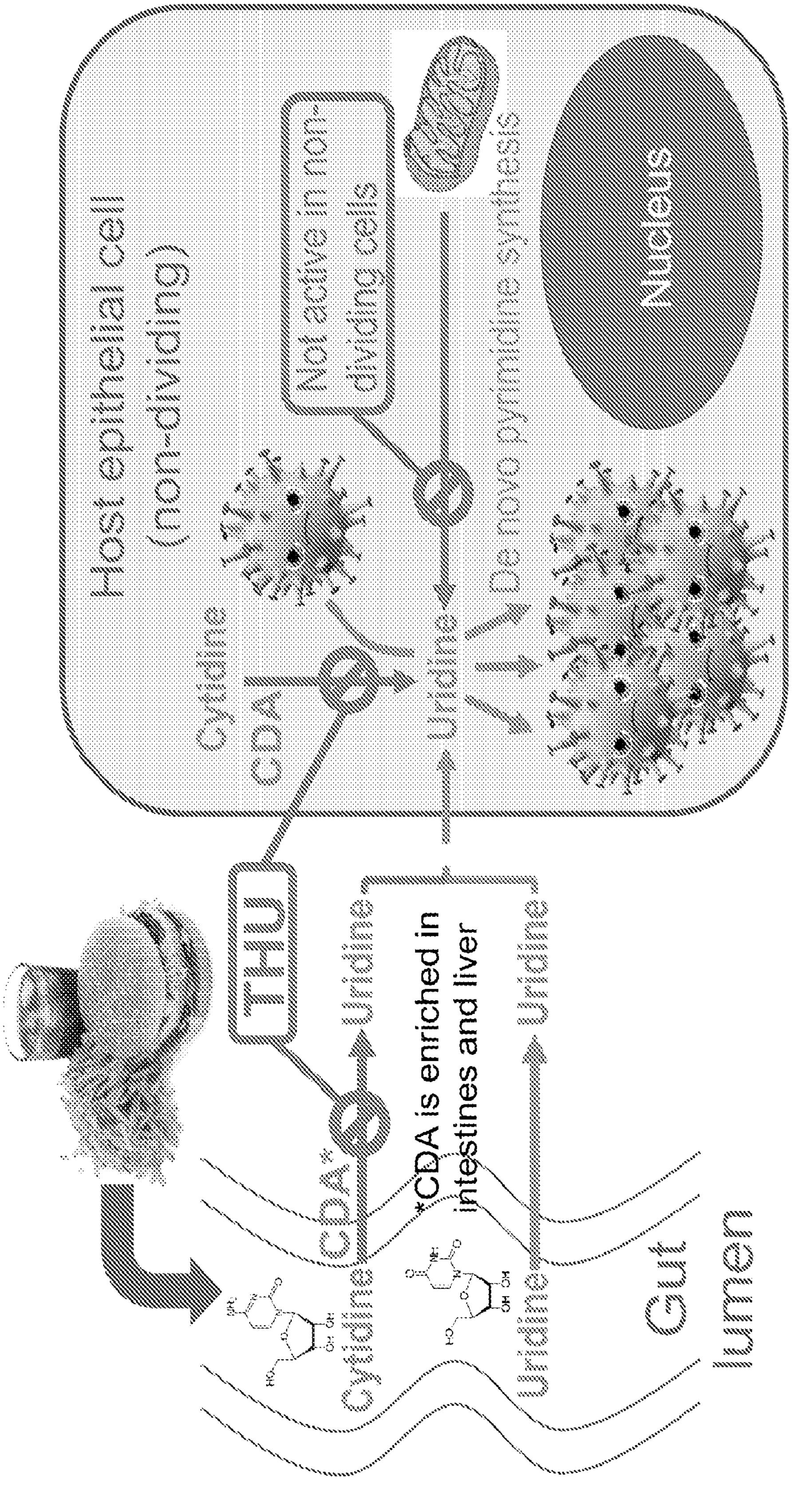
FIG. 12 shows host cell uridine is supplied via 4 routes. The most important route in dividing cells is de novo pyrimidine synthesis, that is activated by cell division (by MYC). But SARS-COV-2 target cells are non-dividing epithelial cells: CDA mediates 2 of the 3 uridine supply routes in non-dividing cells. By inhibiting these 2 uridine supply routes, THU decreases uridine availability to non-dividing cells by as much as ~90%, without known immunosuppressing or other side-effects.

Other drugs that decrease host cell uridine are scientifically and clinically validated to inhibit replication of SARS2 and other RNA viruses 16-24, but THU has advantages. Host cell uridine is supplied via 4 routes: in dividing cells, the most important source is de novo synthesis from glutamine and aspartate basic building blocks, rate-limited by the enzyme DHODH. The generic drugs teriflunomide and its pro-drug leflunomide (approved to treat multiple sclerosis and rheumatoid arthritis respectively) are DHODH inhibitors that decrease uridine amounts in actively proliferating cells: DHODH inhibitors are reproducibly documented to inhibit replication of diverse viruses including SARS2 in vitro (assays conducted in exponentially proliferating cells) (FIG. 10—data from Xiong et al. (2020). Novel and Potent Inhibitors Targeting DHODH, a Rate-Limiting Enzyme in De Novo Pyroadine Biosynthesis, Are Broad-Spectrum Antiviral against RNA Viruses Including Newly Emerged Coronavirus SARS-COV-2, bioRxiv 11, 983056). Moreover, in several case series of renal transplantation patients infected by CMV, leflunomide cleared virus and/or produced clinical improvement (n=4, 2517, 26 and 3127) (27-30). One major limitation of inhibiting de novo synthesis in this way, however, is toxicity to proliferating host cells, e.g., immune cells and recovering epithelial tissue. There is another critical limitation, however, that has not previously been addressed: non-dividing host cells, e.g., respiratory epithelial cells infected by SARS2 (34), do not rely on de novo synthesis of nucleobases from basic building blocks such as glutamine. Instead, these non-dividing cells salvage nucleobases from the extra-cellular space (FIG. 11, 12). Thus, inhibitors of host cell de novo nucleotide synthesis may suppress immunity/tissue-repair but not SARS2 replication. This limitation is difficult to recognize in pre-clinical in vitro studies, which use, for practical technical reasons, exponentially proliferating cells (e.g., A549 lung cancer cells), but this limitation will likely undermine in vivo treatment of a virus, e.g., SARS2, that targets non-dividing epithelial cells. As such, THU may be a better broad-spectrum anti-viral treatment.

THU can be rationally combined with other anti-viral drugs. Although THU has not previously been evaluated as a separate entity for treatment of viral (or other) disease, it has been used in several pre-clinical studies to block the metabolism of co-administered anti-viral cytidine analogs, e.g., pyrimidine nucleoside analogs to inhibit viral polymerases (9-13). In certain embodiments, THU is combined with remdesivir for treatment of RNA viral infection. In other embodiments, THU is combined with a de novo pyrimidine synthesis inhibitor (e.g., teriflunomide, which is approved to treat multiple sclerosis), since the combination more profoundly depletes host cell uridine bases (shown previously in exponentially proliferating cells (46)) to potentially curtail viral replication more broadly, yet permit a reduction in teriflunomide dose and/or duration to spare immunity (Table 2).

TABLE 2

Summarized rationale for THU single-agent and combination with teriflunomide (or remdesivir, not shown in this table, to treat SARS2 or other viruses).

| Rationale | Teriflunomide | THU | Teriflunomide + THU |
|---|---|---|---|
| Decrease UTP availability in dividing cells | Yes (more profoundly in combination with THU) | Partial | Yes (profound) |
| Decrease UTP availability in non-dividing cells | No | Yes | Yes |
| Non-immunosuppressive | No (mild/ moderate) | Yes | No (mild/ moderate) |
| Well established clinical PK/PD | Yes | Yes | Yes |
| Well established clinical safety | Yes | Yes (safe ebough for post-exposure prophylasxis) | No data (↓teriflunomide duration to ↓ immune-suprression) |
| Oral route of administration | Yes | Yes | Yes |
| Broad-spectrum anti-viral | Yes | Yes | Yes |

REFERENCES:

1. Shen et al. Proteomic and Metabolomic Characterization of COVID-19 Patient Sera. Cell. 2020; 182(1):59-72 e15.
2. Hagemeijer et al., Visualizing coronavirus RNA synthesis in time by using click chemistry. J Virol. 2012; 86(10):5808-5816.

3 Ho et al. Effects of tetrahydrouridine on the uptake and metabolism of 1-beta-D-arabinofuranosylcytosine in human normal and leukemic cells. Cancer Res. 1980; 40(7):2444-2446.

4. Lavelle et al. Effects of tetrahydrouridine on pharmacokinetics and pharmacodynamics of oral decitabine. Blood. 2012: 119(5): 1240-1247.

5. Molokie et al. Oral tetrahydrouridine and decitabine for non-cytotoxic epigenetic gene regulation in sickle cell disease: A randomized phase 1 study. PLOS Med. 2017:14(9):e1002382.

6. Simmonds P. Rampant C→U Hypermutation in the Genomes of SARS-COV-2 and Other Coronaviruses: Causes and Consequences for Their Short- and Long-Term Evolutionary Trajectories. mSphere. 2020:5(3).

7. Heinemann and Plunkett, Modulation of deoxynucleotide metabolism by the deoxycytidylate deaminase inhibitor 3,4,5,6-tetrahydrodeoxyuridine. Biochem Pharmacol. 1989:38(22): 4115-4121.

8. Cao et al. A Trial of Lopinavir-Ritonavir in Adults Hospitalized with Severe Covid-19. N Engl J Med. 2020.

9 Aduma et al., Regulatory effects of deoxyribonucleosides on the activity of 5-methoxymethyl-2'-deoxycytidine: modulation of antiherpes activity by deoxyguanosine and tetrahydrodeoxyuridine. Antiviral Res. 1991:15(4):301-313.

10. Aduma et al., Deoxyribonucleoside triphosphate pools of herpes simplex virus infected cells: the influence of selective antiherpes agents and the role of the deaminase pathway. Biochem Cell Biol. 1991:69(5-6): 409-414.

11. Schat et al., Cell-specific antiviral activity of 1-(2-fluoro-2-deoxy-beta-D-arabinofuranosyl)-5-iodocytosine (FIAC) against Marek's disease herpesvirus and turkey herpesvirus. Antiviral Res. 1984; 4(5):259-270.

12. Shannon et al., Evaluation of carbodine, the carbocyclic analog of cytidine, and related carbocyclic analogs of pyrimidine nucleosides for antiviral activity against human influenza Type A viruses. Antimicrob Agents Chemother. 1981; 20(6):769-776.

13. North and Mathews Tetrahydrouridine specifically facilitates deoxycytidine incorporation into herpes simplex virus DNA. J Virol. 1981; 37(3):987-993.

14. Zhao et al. Antagonism of the interferon-induced OAS-RNase L pathway by murine coronavirus ns2 protein is required for virus replication and liver pathology. Cell Host Microbe. 2012; 11(6):607-616.

15. Gu et al. Decitabine- and 5-azacytidine resistance emerges from adaptive responses of the pyrimidine metabolism network. Leukemia. 2020.

16. Totura and Bavari, Broad-spectrum coronavirus antiviral drug discovery. Expert Opin Drug Discov. 2019: 14(4):397-412.

17. Zumla et al., Coronaviruses—drug discovery and therapeutic options. Nat Rev Drug Discov. 2016:15(5): 327-347.

18. Gil-Fernandez et al., Antiviral activity of uridine 5'-diphosphate glucose analogues against some enveloped viruses in cell culture. Antiviral Res. 1987:8(5-6):299-310.

19. Krol et al., Antiviral Activity of Uridine Derivatives of 2-Deoxy Sugars against Tick-Borne Encephalitis Virus. Molecules. 2019; 24(6).

20. Camarasa et al. Uridine 5'-diphosphate glucose analogues. Inhibitors of protein glycosylation that show antiviral activity. J Med Chem. 1985; 28(1):40-46.

21. Barnard et al. Inhibition of severe acute respiratory syndrome-associated coronavirus (SARSCOV) by calpain inhibitors and beta-D-N4-hydroxycytidine. Antivir Chem Chemother. 2004:15(1): 15-22.

22. Chen et al. Suppression of pyrimidine biosynthesis by targeting DHODH enzyme robustly inhibits rotavirus replication. Antiviral Res. 2019:167:35-44.

23. Chung D. The Establishment of an Antiviral State by Pyrimidine Synthesis Inhibitor is Cell Type-Specific. J Antimicrob Agents. 2015: 1(1).

24. Ortiz-Riano et al., Inhibition of arenavirus by A3, a pyrimidine biosynthesis inhibitor. J Virol. 2014:88(2): 878-889.

25. Denison et al., Coronaviruses: an RNA proofreading machine regulates replication fidelity and diversity. RNA Biol. 2011; 8(2):270-279.

26. Knight et al., Inhibition of herpes simplex virus type 1 by the experimental immunosuppressive agent leflunomide. Transplantation. 2001; 71(1): 170-174.

27. Chong et al., Concurrent antiviral and immunosuppressive activities of leflunomide in vivo. Am J Transplant. 2006; 6(1):69-75.

28. John et al., Leflunomide therapy for cytomegalovirus disease in renal allograft recepients. Transplantation. 2004:77(9): 1460-1461.

29. John et al., A prospective evaluation of leflunomide therapy for cytomegalovirus disease in renal transplant recipients. Transplant Proc. 2005:37(10):4303-4305.

30. Morita et al., Successful low-dose leflunomide treatment for ganciclovir-resistant cytomegalovirus infection with high-level antigenemia in a kidney transplant: A case report and literature review. J Clin Virol. 2016: 82: 133-138.

31. Ng et al., Clinical Pharmacokinetic Monitoring of Leflunomide in Renal Transplant Recipients with BK Virus Reactivation: A Review of the Literature. Clin Pharmacokinet. 2017:56(9): 1015-1031.

32. Bernhoff et al., Leflunomide inhibition of BK virus replication in renal tubular epithelial cells. J Virol. 2010:84(4):2150-2156.

33. Liacini et al., Anti-BK virus mechanisms of sirolimus and leflunomide alone and in combination: toward a new therapy for BK virus infection. Transplantation. 2010; 90(12): 1450-1457.

34. Hou et al. SARS-COV-2 Reverse Genetics Reveals a Variable Infection Gradient in the Respiratory Tract. Cell. 2020:182(2):429-446 e414.

35. Ferraris et al. Design, synthesis, and pharmacological evaluation of fluorinated tetrahydrouridine derivatives as inhibitors of cytidine deaminase. J Med Chem. 2014:57(6): 2582-2588.

36. Kreis et al., Tetrahydrouridine: Physiologic disposition and effect upon deamination of cytosine arabinoside in man. Cancer TreatRep. 1977:61(7): 1347-1353.

37. Terse et al. Subchronic oral toxicity study of decitabine in combination with tetrahydrouridine in CD-1 mice. Int J Toxicol. 2014; 33(2):75-85.

38. Ho et al. Clinica, pharmacology of tetrahydrouridine. JClinPharmacol. 1978:18(5-6):259-265.

39. Goldenthal et al., Preclinical toxicologic evaluation of tetrahydrouridine (NSC-112907) in beagle dogs and rhesus monkeys. Cancer ChemotherRep3. 1974; 5(1): 15-16.

40. DeSimone et al., Tetrahydrouridine, cytidine analogues, and hemoglobin F. AmJHematol. 1985:18(3): 283-288.

41. Riccardi et al., Influence of tetrahydrouridine on the pharmacokinetics of intrathecally administered 1-beta-D-arabinofuranosylcytosine. Cancer Res. 1982:42(5): 1736-1739.
42. Kreis et al. Therapy of refractory/relapsed acute leukemia with cytosine arabinoside plus tetrahydrouridine (an inhibitor of cytidine deaminase)—a pilot study. Leukemia. 1991:5(11): 991-998.
43. Dover et al., 5-Azacytidine increases HbF production and reduces anemia in sickle cell disease: dose-response analysis of subcutaneous and oral dosage regimens. Blood. 1985:66(3):527-532.
44. Wong et al. Phase I evaluation of tetrahydrouridine combined with cytosine arabinoside. Cancer TreatRep. 1979:63(8): 1245-1249.
45. Poulain et al., Footprint of the host restriction factors $APOBEC_3$ on the genome of human viruses. PLOS Pathog. 2020; 16(8):e1008718.
46. Schwartsmann et al. DUP 785 (NSC 368390): schedule-dependency of growth-inhibitory and antipyrimidine effects. Biochem Pharmacol. 1988:37(17):3257-3266.
47. Beumer et al. Plasma pharmacokinetics and oral bioavailability of 3,4,5,6-tetrahydrouridine, a cytidine deaminase inhibitor, in mice. Cancer ChemotherPharmacol. 2008:62(3): 457-464.
48. Marsh et al., Therapy of refractory/relapsed acute myeloid leukemia and blast crisis of chronic myeloid leukemia with the combination of cytosine arabinoside, tetrahydrouridine, and carboplatin. Cancer Chemother-Pharmacol. 1993:31(6): 481-484.
49. Newman et al., A phase I, pharmacokinetic, and pharmacodynamic evaluation of the DNA methyltransferase inhibitor 5-fluoro-2'-deoxycytidine, administered with tetrahydrouridine. Cancer Chemother Pharmacol. 2015:75(3):537-546.
50. Drappier et al., A novel mechanism of RNase L inhibition: Theiler's virus L* protein prevents 2-5A from binding to RNase L. PLOS Pathog. 2018; 14(4): e1006989.
51. Jha et al., Suppression of antiviral innate immunity by sunitinib enhances oncolytic virotherapy. Mol Ther. 2013; 21(9): 1749-1757.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating a subject infected with an RNA virus without suppressing immunity comprising:

administering a composition to lungs of a subject via said subject's airway, or providing said composition to said subject such that said subject administers said composition to said lungs themselves via said airway;

wherein said lungs have non-dividing epithelial cells infected with SARS-COV-2 or other coronavirus;

wherein said composition is non-immuno-suppressing and comprises a cytidine deaminase inhibitor.

2. The method of claim 1, wherein said cytidine deaminase inhibitor comprises tetrahydrouridine, cedazuridine, and/or diazepinone riboside.

3. The method of claim 1, wherein said cytidine deaminase inhibitor comprises a compound of Formula I, wherein Formula I is as follows:

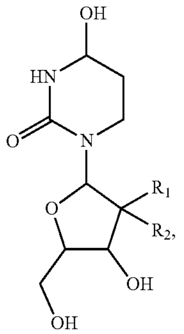

or a pharmaceutically acceptable salt of the compound, wherein:

$R_1$ and $R_2$ are independently selected from the group consisting of hydrogen, halo, cyano, nitro, sulfhydryl, hydroxyl, formyl, carboxyl, COO ($C_1$ to $C_6$ straight or branched chain alkyl), COO ($C_1$ to $C_6$ straight or branched chain alkenyl), COO ($C_1$ to $C_6$ straight or branched chain alkynyl), CO ($C_1$ to $C_6$ straight or branched chain alkyl), CO ($C_1$ to $C_6$ straight or branched chain alkenyl), CO ($C_1$ to $C_6$ straight or branched chain alkynyl), $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy;

wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy, may be independently unsubstituted or substituted with one to four substituents independently selected from the group consisting of halo, hydroxyl, cyano, nitro, formyl, carboxyl, and sulfhydryl;

and provided that when one of $R_1$ and $R_2$ is —H, then the other is not —H, —OH or —$CH_2OH$.

4. The method of claim 1, wherein said RNA virus is SARS-COV-2.

5. The method of claim 1, wherein said subject is further administered an inhibitor of viral RNA polymerase.

6. The method of claim 5, wherein said inhibitor of viral RNA polymerase is remdesivir.

7. The method of claim 1, wherein said subject is a human.

8. The method of claim 1, wherein said subject is an animal.

9. The method of claim 1, wherein said administering is such that said subject receives about 5-100 mg of said cytidine deaminase inhibitor per kilogram of said subject per day.

10. The method of claim 1, further comprising: administering or providing an anti-coagulant to said subject.

11. The method of claim 1, wherein said subject is on a ventilator.

12. The method of claim 1, wherein said composition further comprises a physiologically tolerable buffer.

* * * * *